US005713921A

United States Patent [19]
Bonutti

[11] Patent Number: 5,713,921
[45] Date of Patent: Feb. 3, 1998

[54] SUTURE ANCHOR

[76] Inventor: Peter M. Bonutti, 1303 W. Evergreen Plz., Effingham, Ill. 62401

[21] Appl. No.: 626,393

[22] Filed: Mar. 29, 1996

[51] Int. Cl.$^6$ ...................................................... A61B 17/04
[52] U.S. Cl. .................................................................. 606/232
[58] Field of Search ............................... 606/232, 60, 64, 606/184, 72, 73, 139

[56] References Cited

U.S. PATENT DOCUMENTS

| 5,269,809 | 12/1993 | Hayhurst et al. | 606/232 |
| 5,403,348 | 4/1995 | Bonutti. | |
| 5,488,958 | 2/1996 | Topel et al. | 128/754 |
| 5,540,718 | 7/1996 | Bartlett | 606/232 |
| 5,626,612 | 5/1997 | Barlett | 606/232 |

Primary Examiner—Michael Buiz
Assistant Examiner—Tina T. D. Pham
Attorney, Agent, or Firm—Tarolli, Sundheim, Covell, Tummino & Szabo

[57] ABSTRACT

An improved suture anchor is formed from body tissue. The body tissue is shaped to a desired configuration for the anchor and defines a passage through the anchor. A suture is inserted into the passage in the body tissue of the anchor. The anchor is then positioned in a patient's body with a suture extending into the passage in the anchor. The anchor may be formed of osseous body tissue, hard compact bone, dense connective body tissue, or other body tissue. The body tissue may be dried so that it absorbs fluid and expands upon being inserted into a patient's body.

52 Claims, 3 Drawing Sheets

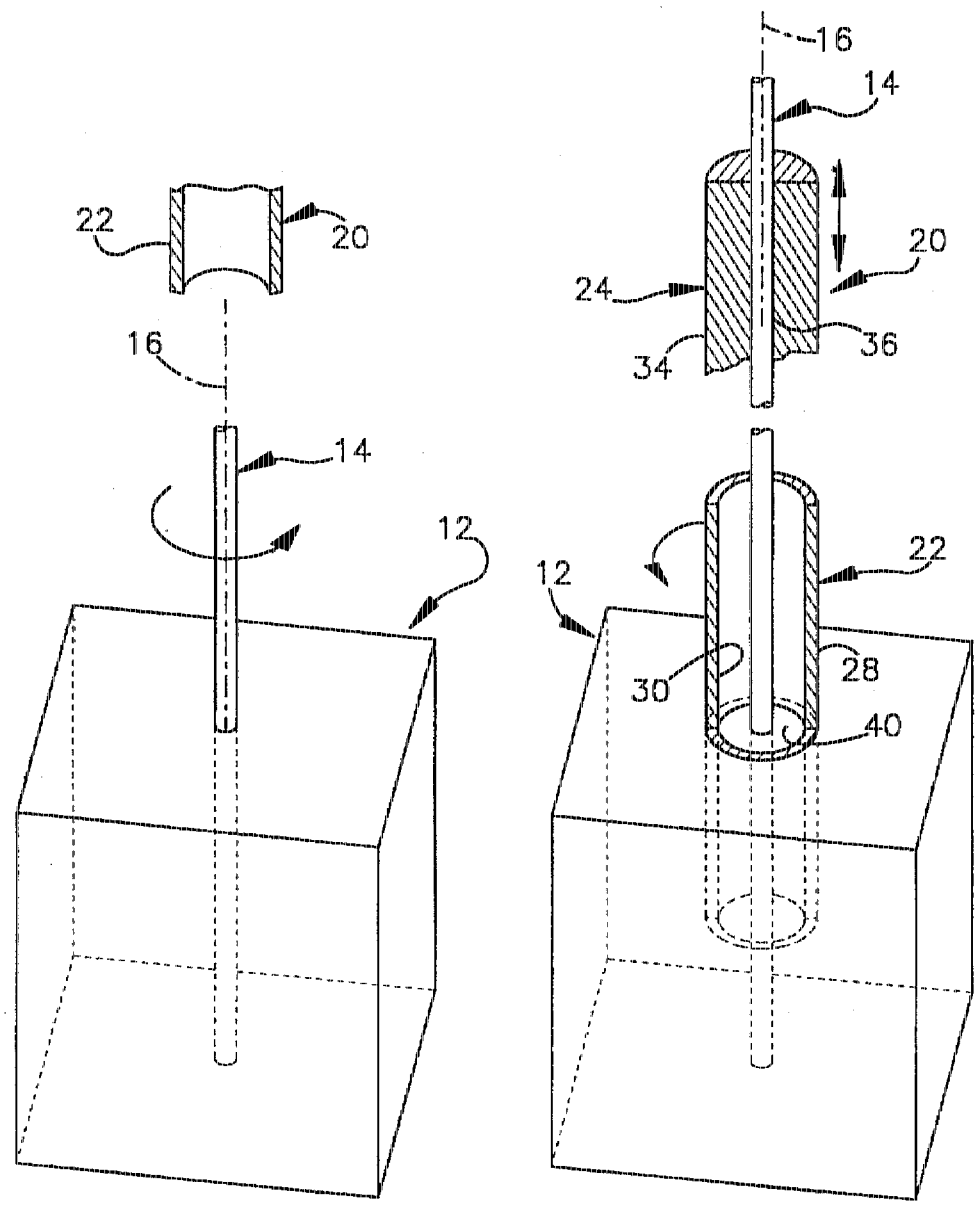
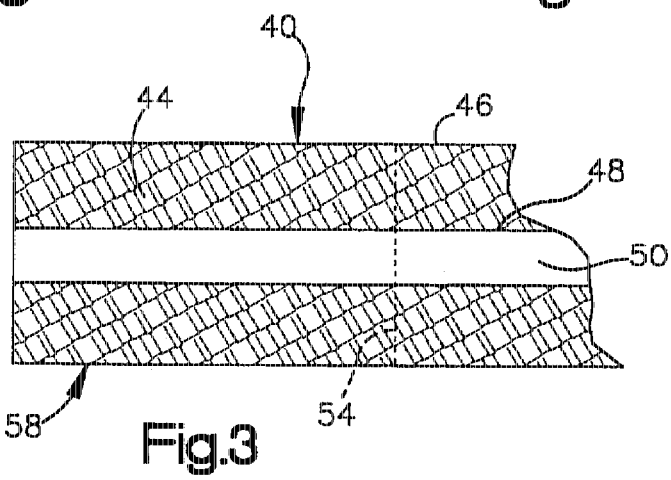
Fig.1　　Fig.2
Fig.3

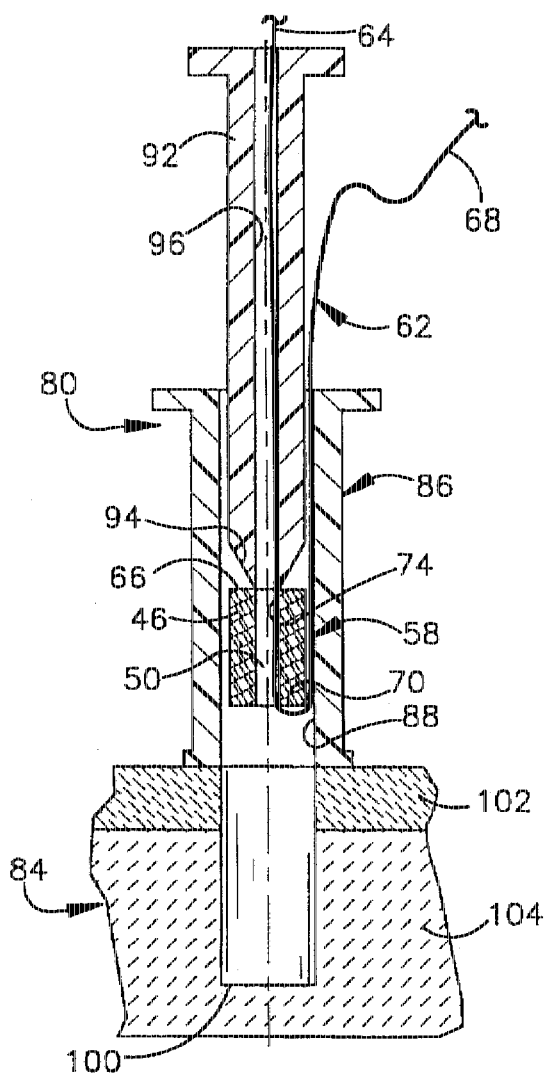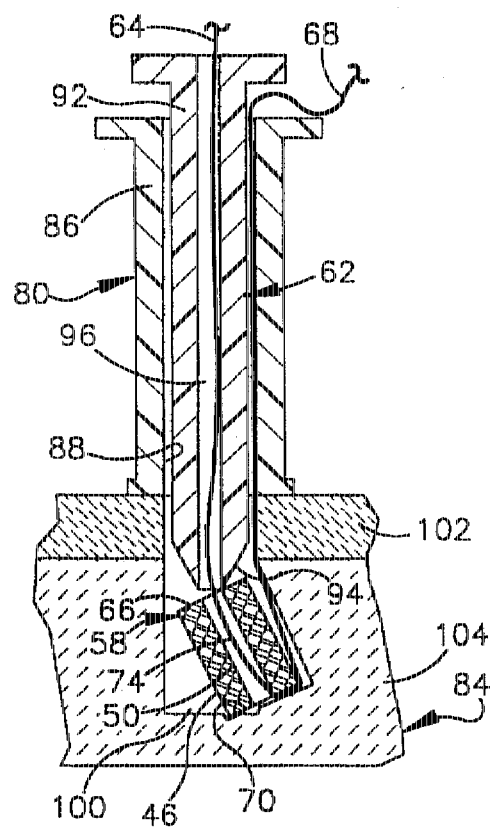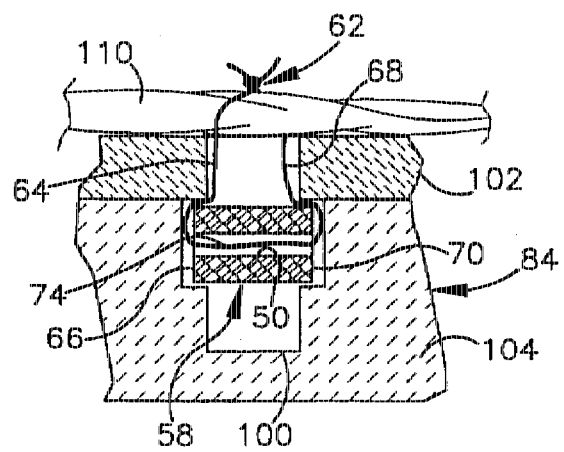

SUTURE ANCHOR

BACKGROUND OF THE INVENTION

The present invention relates to a new and improved suture anchor and more specifically to a suture anchor which is formed of body tissue.

Anchors are commonly utilized to retain sutures in a patient's body. The anchors have previously been formed of metal, such as stainless steel or titanium. In addition, anchors have been formed of biodegradable materials. While being generally satisfactory, these known anchors have the drawback that they are material which is not body tissue and are inserted into a patient's body. It has previously been suggested to construct anchors in the manner disclosed in U.S. Pat. Nos. 5,405,359; 5,403,348; 5,203,787; 5,046,513; and 5,041,129.

SUMMARY OF THE INVENTION

The present invention relates to a new and improved suture anchor which is formed of body tissue. The body tissue is shaped to the desired configuration of the anchor. The body tissue defines a passage through the anchor. A suture is inserted into the passage in the anchor. The anchor and the suture are inserted into a patient's body.

The anchor may be formed of many different types of body tissue, including osseous body tissue, bone, or dense connective tissue. The body tissue may be dried so that when the anchor is exposed to fluid in a patient's body, the anchor absorbs the fluid and expands. The body tissue may be from the patient's body, from another human, or from a non-human animal.

BRIEF DESCRIPTION OF THE DRAWINGS

The foregoing and other features of the invention will become more apparent upon a consideration of the following description taken in connection with the accompanying drawings, wherein:

FIG. 1 is a schematic illustration depicting the manner in which a thin elongated member is inserted into body tissue;

FIG. 2 is a schematic illustration, generally similar to FIG. 1, illustrating the manner in which a cutting tool is moved axially along the thin elongated member into the body tissue;

FIG. 3 is an enlarged schematic illustration of body tissue formed with the thin elongated member and cutting tool of FIGS. 1 and 2;

FIG. 4 is a schematic illustration depicting the manner in which an anchor formed of the body tissue of FIG. 3 is inserted into a patient's body with a suture extending into the anchor;

FIG. 5 is a schematic illustration depicting the manner in which the anchor of FIG. 4, formed of body tissue, is pivoted in a patient's body;

FIG. 6 is a schematic illustration depicting the manner in which the patient's body tissue is secured with a suture which extends into the anchor formed of body tissue;

DESCRIPTION OF SPECIFIC PREFERRED EMBODIMENTS OF THE INVENTION

General Description

Figure 7:
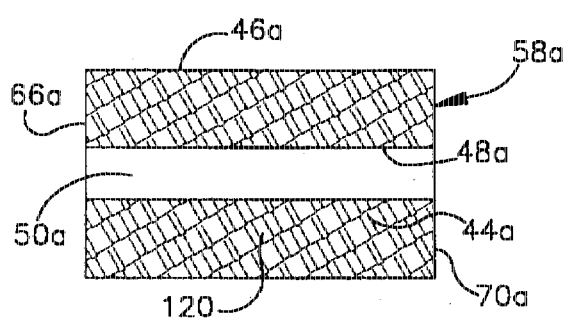
FIG. 7 is a sectional view of an anchor formed of dense connective body tissue.

Suture anchors have previously been utilized to retain sutures in either hard or soft tissue in a human patient's body. The suture anchors have previously been formed of metal, biodegradable materials, and other materials which do not naturally occur in a patient's body. The insertion of materials other than body tissue into a patient's body may be objectionable.

In accordance with a feature of the present invention, sutures are retained in a patient's body by anchors formed of body tissue. In one specific embodiment of the invention, the anchor is formed of bone or osseous (bonelike) tissue. In another embodiment of the invention, the anchor is formed of dense connective body tissue. The dense connective body tissue may contain collagen. The dense connective body tissue may be cartilage, tendon or ligament. The dense connective body tissue may be interarticular fibrocartilage which previously formed a meniscus in a joint. Although it is believed that it may be preferred to use bone, osseous tissue, or dense connective tissue to form the anchor, other body tissue may be utilized if desired.

It is contemplated that the body tissue which is used to form the anchor may be dried. When an anchor formed of dried body tissue is inserted into a patient's body at a location where it is exposed to the fluids in the patient's body, the anchor absorbs the body fluid and expands. As the anchor expands, it presses against the surrounding tissue in the patient's body and becomes firmly interlocked with the surrounding tissue of the patient's body.

It is contemplated that the body tissue forming the anchor may be dried in many different known ways. Specifically, the body tissue may be dried by placing it in a press and applying pressure against the body tissue to force fluid from the body tissue. Alternatively, the body tissue may be freeze dried or dried by exposure to a relatively warm dry environment. The dried body tissue which forms the anchor may be bone, osseous tissue, dense connective tissue, or other body tissue. For example, the dried body tissue forming the anchor could be formed of dried skin or other soft tissue and be used to retain a suture in soft body tissue.

It is contemplated that the body tissue used to form the anchor may be the patient's own body tissue (autograft). It is believed that this has the advantage of minimizing the remote possibility of infecting a patient with the material of the anchor. However, the body tissue forming the anchor may be obtained from another human patient (allograft) or from a non-human animal, such as a bovine animal (xenograft).

It is contemplated that an anchor formed of body tissue in accordance with the present invention may have many different configurations. Thus, the anchor may have a polygonal configuration or a generally spherical configuration. However, it is believed that it may be preferred to form the anchor with a cylindrical configuration and with a passage to receive a portion of a suture.

When an anchor is to be formed, a thin elongated member may be inserted into body tissue. The thin elongated member is used to guide a cutting tool as it moves into the body tissue. The cutting tool forms a cylindrical outer side surface of the anchor. The thin elongated member forms a passage which extends through the anchor. Although this method of forming the anchor may be preferred, it is contemplated that other methods of forming the anchor could be utilized if desired. For example, the body tissue may be shaped with a press or molded to a desired configuration.

Anchor Formed of Bone or Osseous Body Tissue

Body tissue 12 is illustrated schematically in FIG. 1. The body tissue 12 may be disposed within a human patient's body or may be separate from the patient's body. The body tissue 12 may be the patient's own body tissue or may be body tissue from another human patient. Alternatively, the body tissue 12 may be from a non-human animal, such as a bovine animal. Although the body tissue 12 has been illustrated in FIG. 1 as having a polygonal configuration, the body tissue 12 may have any desired configuration. When the body tissue 12 is disposed within a patient's body, it is contemplated that the body tissue will have a configuration corresponding to the configuration of a naturally occurring portion of the patient's body.

The body tissue 12 may be natural or artificial bone or osseous body tissue. In the embodiment of the invention illustrated in FIG. 1, the body tissue 12 is hard compact human bone of the type which encloses soft cancellous bone. The bone forming the body tissue 12 may be a bone in the body of the human patient, for example, a portion of a femur of a patient. However, in FIG. 1, the body tissue 12 is illustrated as being spaced from the patient's body.

When a suture anchor is to be formed from the body tissue 12, a thin elongated metal member 14 is inserted into the hard compact human bone. The thin elongated member 14 may be a K-wire or similar article. The thin elongated member 14 is inserted into the hard bony body tissue 12 by rotating the thin elongated member about its longitudinal central axis 16 and pressing a leading end of the thin elongated member against the body tissue.

The leading end of the thin elongated member 14 may be pointed or may have a flat circular configuration. If desired, the leading end of the thin elongated member 14 may be provided with a cutting edge, similar to a cutting edge used on a drill. Although it is preferred to rotate the thin elongated member 14 as it is inserted into the hard compact bone 12, with other body tissue, the thin elongated member may be inserted without being rotated about its central axis.

In the illustrated embodiment of the thin elongated member 14, the thin elongated member has a cylindrical outer side surface with a diameter which corresponds to the desired diameter of a passage to be formed in a suture anchor formed of the body tissue 12. In the procedure illustrated in FIG. 1, the thin elongated member 14 is rotated about the axis 16 and pushed completely through the piece of body tissue 12. However, if desired, the thin elongated member 14 could be moved only part way through the body tissue 12. For example, when the body tissue 12 is disposed within a patient's body, it is contemplated that the thin elongated member 14 may not be inserted completely through the portion of the patient's body formed by the body tissue.

Once the thin elongated member 14 has been inserted into the body tissue 12, in the manner illustrated in FIG. 1, a rotating metal cutting tool 20 is moved axially along the thin elongated member 14 into the body tissue. The cutting tool 20 has a leading or cutting portion 22 (FIG. 2) and a trailing or guiding portion 24. The cutting portion 22 of the cutting tool 20 has a tubular cylindrical configuration. Thus, the leading or cutting portion 22 of the cutting tool 20 has a cylindrical outer side surface 28 and a cylindrical inner side surface 30. The cutting portion 22 of the cutting tool 20 has a leading end portion which may form a portion of a cone or which may have cutting teeth to promote a cutting action as the cutting tool is rotated and moved axially along the thin elongated member 14.

The trailing or guiding portion 24 of the cutting tool 20 has a cylindrical outer side surface 34. The outer side surface 34 forms a continuation of the cylindrical outer side surface 28 of the leading or cutting portion 22 of the cutting tool. In addition, the trailing or guiding portion 24 of the cutting tool 20 has a cylindrical inner side surface 36. The inner side surface 36 engages and is freely movable relative to the cylindrical outer side surface of the thin elongated member 14.

The cylindrical inner side surface 36 of the guiding portion 24 of the cutting tool 20 engages the cylindrical outer side surface of the thin elongated member 14. This enables the guiding portion 24 to maintain the leading or cutting portion 22 of the rotating cutting tool 20 in a coaxial relationship with the thin elongated member 14. Although it is preferred to rotate the cutting tool 20 as it is moved into the hard compact bone 12, with other body tissue, the cutting tool may be inserted without being rotated about its central axis 16.

After the thin elongated member 14 has been inserted into the body tissue 12, in the manner illustrated in FIG. 1, the cutting tool 20 is moved into telescopic engagement with the thin elongated member. The cutting tool 20 is rotated about the central axis 16 of the thin elongated member by an electric or pneumatic motor or similar device. As the cutting tool 20 is rotated about the longitudinal central axis 16 of the thin elongated member 14, the cutting tool is moved axially along the thin elongated member into engagement with the body tissue 12.

AS the leading or cutting portion 22 of the rotating cutting tool 20 moves into engagement with the body tissue 12, the cutting portion cuts a very thin annular groove around the thin elongated member 14 in a coaxial relationship with the thin elongated member. As the cutting tool 20 moves axially into the body tissue 12, a cylindrical core 40 of body tissue is cut from the block of bone. The cylindrical core 40 of body tissue is disposed within the tubular leading end portion 22 of the cutting tool 20. Once a core 40 of a desired axially extent has been cut in the body tissue 12, the cutting tool 20 is moved upward (as viewed in FIG. 2) along the thin elongated member and out of engagement with the body tissue 12. The core 40 is then removed from the remaining body tissue 12.

The core 40 (FIG. 3) has a tubular cylindrical configuration. The cylindrical core 40 has a tubular wall 44 formed of the body tissue 12. The tubular wall 44 has a cylindrical outer side surface 46 which is coaxial with a cylindrical inner side surface 48. The cylindrical outer side surface 46 has a diameter corresponding to the desired outside diameter of a suture anchor. The cylindrical outer side surface 46 of the tubular side wall 44 was formed by and has the same diameter as the inner side surface 30 of the cutting portion 22 of the cutting tool 20.

The cylindrical inner side surface 48 of the core 40 has a diameter corresponding to the diameter of the cylindrical outer side surface of the thin elongated member 14. The cylindrical inner side surface 48 forms a passage 50 which extends axially through the cylindrical core 40. The tubular side wall 44 of the cylindrical core 40 is formed as one piece of the body tissue 12.

The core 40 has an axial extent which is greater than the desired axial extent of a suture anchor. Therefore, the core 40 is cut, along a line indicated at 54 in FIG. 3, to form a suture anchor 58 with a desired axial extent. Although the core 40 may be cut or ground to form an anchor 58 with any one of many different axially tapering or flaring configurations, such as those disclosed in U.S. Pat. No.

5,403,348, it is believed that it may be preferred to form the anchor 58 with a cylindrical configuration.

Although it is contemplated that the tubular cylindrical suture anchor 58 could be of many different sizes, it is believed that the suture anchor may preferably have a length or axial extent of between 2 and 4 millimeters. The cylindrical outer side surface 46 of the suture anchor 58 may have a diameter of between 1 and 2 millimeters. The cylindrical inner side surface 48 of the passage 50 in the suture anchor 58 may have a diameter of ½ to 1 millimeters. Of course, the suture anchor 58 could be formed with different dimensions if desired.

Since the volume of body tissue which is required to form the suture anchor 58 is relatively small, the bone which forms the suture anchor 58 can be removed from a patient's own body with minimal detrimental effect to the patient. Thus, the thin elongated member 14 may be inserted into a bone in a patient's body. The cutting tool 20 would then be used to cut the bone in the patient's body. Of course, if desired, the body tissue for the suture anchor 58 could be obtained from another source, such as another human or from a non-human animal.

Once the suture anchor 58 has been formed from the body tissue 12, a suture 62 (FIG. 4) is inserted into the passage 50 in the suture anchor 58. The suture 62 includes a portion or leg 64 which extends away from an annular end surface 66 of the anchor 58. In addition, the suture 62 has a second portion or leg 68 which extends across an annular end surface 70 of the anchor 58. The leg 68 of the suture 62 extends along the cylindrical outer side surface 46 of the anchor 58 to a location adjacent to and spaced from the leg portion 64 of the suture 62. A relatively short portion 74 of the suture 62 interconnects the leg portions 64 and 68 and is disposed in the passage 50 in the suture anchor 58.

An inserter assembly 80 is used to position the suture anchor 58 and a portion of the suture 62 in a patient's body tissue 84. The inserter assembly 80 includes a cylindrical tubular outer sleeve 86 having a central passage 88 in which the anchor 58 is disposed. The inserter 80 also includes a tubular inner sleeve 92 which is telescopically received in the outer sleeve 86. The tubular inner sleeve 92 has a bevelled leading end portion 94 which engages the trailing end surface 66 of the anchor 58.

The leg or portion 64 of the suture 62 extends through a cylindrical passage 96 in the inner sleeve 92. The leg or portion 68 of the suture 62 extends through the central passage 88 in the outer sleeve 86 along a path which extends between the inner and outer sleeves. However, if desired, one of the legs or portions 64 or 68 of the suture could be omitted. If this was done, the suture 62 could be tied off at one end of the anchor 58.

It is contemplated that the anchor 58 may be inserted into a human patient's body at may different locations. The anchor 58 may be inserted into either hard or soft tissue. In the situation illustrated schematically in FIG. 4, the anchor 58 is being inserted into bone tissue 84 in a patient's body. A recess 100 is formed in the bone tissue 84 of the human patient's body by drilling or other methods. The recess 100 extends through the hard compact outer layer 102 of the patient's bone tissue 84 into the relatively porous inner or cancellous tissue 104. The illustrated anchor 58 is formed of the same bone as the hard outer layer 102.

To insert the anchor 58 in the patient's body tissue 84, the inner sleeve 92 is moved axially downward (as viewed in FIG. 4) to apply force against the trailing annular end surface 66 of the anchor 58. Once the anchor 58 has been pushed into the recess 100 by axial movement of the inner sleeve 92 relative to the outer sleeve 86, the leg 68 of the suture 62 is tensioned to apply force against the leading annular end surface 70 of the anchor 58. At the same time, the bevelled leading end 94 of the inner sleeve 92 is pressed against the trailing end surface 66 of the anchor.

This results in the application of a counterclockwise (as viewed in FIGS. 4 and 5) torque to the anchor 58. This torque causes the anchor to pivot through the orientation shown in FIG. 5 toward the orientation shown in FIG. 6. Once the anchor has been pivoted to the orientation shown in FIG. 6, by tensioning the suture 62 and applying force against the anchor with the leading end portion 94 of the inner sleeve 92, the anchor 58 engages the hard compact outer layer 102 of the patient's bone tissue 84 to hold the anchor in the recess 100.

The suture 68 can then be used to secure body tissue 110 in place. The body tissue 110 may be soft tissue, or a ligament, or a tendon, or other body tissue. If desired, the suture 62 may be used to secure an implant or splint in place relative to the patient's body tissue 84.

One specific known inserter assembly 80 and method of inserting a suture anchor 58 into a patient's body tissue has been illustrated in FIGS. 4–6. This specific inserter assembly and the method of inserting the anchor 58 are the same as is disclosed in U.S. Pat. No. 5,403,348 issued Apr. 4, 1995 and entitled "Suture Anchor". However, it is contemplated that many different known types of inserter assemblies could be utilized to install the suture anchor with many different methods in a patient's body tissue. For example, the inserter assembly and method disclosed in U.S. Pat. No. 5,464,426 issued Nov. 7, 1995 and entitled "Method of Closing Discontinuity in Tissue" could be utilized if desired. Of course, other known apparatus and methods could also be utilized if desired.

In the embodiment of the invention illustrated in FIGS. 1–6, the anchor 58 is formed of hard compact outer bone. However, it is contemplated that the anchor 58 could be formed of osseous body tissue other than hard compact bone. The osseous body tissue could be obtained from the patient or from other sources.

Anchor Formed of Dense Connective Body Tissue

Figure 9:
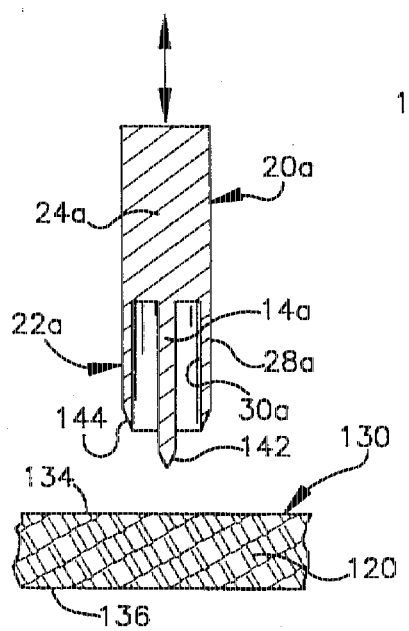
FIG. 9 is a schematic illustration depicting the manner in which a cutting tool is used to cut an anchor from the body tissue shaped with the press of FIG. 8.

In the embodiment of the invention illustrated in FIGS. 1–6, the anchor 58 is formed of osseous tissue. In the embodiment of the invention illustrated in FIGS. 7–9, an anchor is formed of dense connective body tissue. Since the embodiment of the invention illustrated in FIGS. 7–9 is generally similar to the embodiment of the invention illustrated in FIGS. 1–6, similar numerals will be utilized to identify similar components, the suffix letter "a" being associated with the components of FIGS. 7–9 to avoid confusion.

Figure 8:
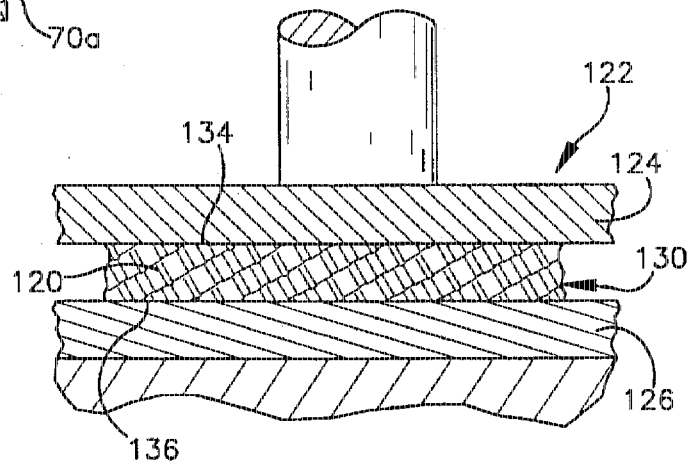
FIG. 8 is a schematic illustration depicting the manner in which dense connective body tissue is shaped in a press.

A suture anchor 58$a$ formed of dense connective body tissue is illustrated in FIG. 7. The suture anchor 58$a$ has the same configuration as the suture anchor 58 of FIGS. 3 and 4. The suture anchor 58$a$ cooperates with a suture in the same manner as in which the suture anchor 58 cooperates with the suture 62 (FIGS. 4–6).

The suture anchor 58$a$ (FIG. 7) has a cylindrical tubular side wall 44$a$ formed of dense connective body tissue. The tubular side wall 44$a$ has a cylindrical outer side surface 46$a$ and a cylindrical inner side surface 48$a$ which extend between axially opposite annular end surfaces 66$a$ and 70$a$ of the suture anchor 58$a$. The cylindrical inner side surface 48$a$ is disposed in a coaxial relationship with the cylindrical outer side surface 46$a$ and defines a passage 50$a$ which extends axially through the suture anchor 58$a$.

Although the suture anchor 58$a$ has a tubular cylindrical configuration, it is contemplated that the suture anchor 58$a$ could have a different configuration if desired. For example, the suture anchor 58a could have a polygonal configuration. If desired, the suture anchor 58a could be formed with a spherical configuration. The suture anchor 58a may have an axially tapering or flaring configuration, similar to the configurations of anchors disclosed in the aforementioned U.S. Pat. No. 5,403,348.

In accordance with a feature of this embodiment of the invention, the suture anchor 58a is formed of dense connective body tissue 120. The dense connective body tissue contains collagen. It is contemplated that the dense connective body tissue 120 may be formed from ligaments or tendon. It is also contemplated that the dense connective body tissue 120 may be formed from cartilage, such as interarticular fibrocartilage which forms a meniscus in a joint. It should be understood that dense connective body tissue other than the specific examples set forth above may be utilized if desired. The dense connective body tissue 120 forming the suture anchor 58a may be removed from a patient's own body. Alternatively, the dense connective body tissue may be obtained from a human other than the patient into which the suture anchor 58a is to be inserted. If desired, the dense connective body tissue 120 could be obtained from a non-human animal, such as a bovine animal. However, it is believed that it may be preferred to use a patient's own dense connective body tissue to form the suture anchor 58a in order to minimize any possibility of infection. If the dense connective body tissue is obtained from a source other than a patient's own body, it may be desired to sterilize the dense connective body tissue using ethylene oxide gas or other sterilizing agents.

Although the dense connective body tissue 120 could be shaped in many different ways, it is preferred to place the dense connective body tissue in a press 122 (FIG. 8). The press 122 has an upper platen 124 which presses the dense connective body tissue 120 against a lower platen 126 to form a flat sheet 130 of dense connective body tissue. The flat sheet 130 has a thickness, as measured perpendicular to parallel flat upper and lower major side surfaces 134 and 136 (FIG. 9) of the flat sheet, which is equal to the desired axial extent of the suture anchor 58a (FIG. 7). Thus, the thickness of the flat sheet 130 is equal to the distance between opposite annular end surfaces 66a and 70a (FIG. 7) of the suture anchor 58a.

A cutting tool 20a (FIG. 9) is used to cut the sheet 130 to form the suture anchor 58a. The cutting tool 130 includes a thin elongated member 14a having a cylindrical outer side surface with a diameter which corresponds to the diameter of the passage 50a in the suture anchor 58a (FIG. 7). In the illustrated embodiment of the cutting tool 20a, a leading end portion 142 of the thin elongated member 14a has a sharp conical configuration. However, if desired, the leading end portion 142 could have a flat circular configuration. Alternatively, the leading end portion 142 of the thin elongated member 14a could have a thin hollow tubular configuration.

The cutting tool 20a has a leading or cutting portion 22a. The leading or cutting portion 22a has a cylindrical outer side surface 28a and a cylindrical inner side surface 30a. The cutting portion 22a of the cutting tool 20a has a sharp leading end portion 144 which is formed as a portion of a right circular cone having a central axis which is coincident with the central axis of the cutting tool 20a and with the central axis of the thin elongated member 14a. A trailing portion 24a of the cutting tool 20a is gripped by a drive device (not shown).

When the suture anchor 58a is to be formed from the sheet 130 of dense connective body tissue 120, the drive device moves the cutting tool 20a straight downward (as viewed in FIG. 9) without rotating the cutting tool. As the cutting tool 20a moves downward, the thin elongated member 14a is inserted into and pierces the sheet 130 of dense connective body tissue 120. Immediately after the leading end portion 142 of the thin elongated member 14a enters the sheet 130 of dense connective body tissue 120, the leading end portion 144 of the cutting portion 22a engages the sheet 130 of dense connective body tissue. Continued downward (as viewed in FIG. 9) movement of the cutting tool 20a results in the cutting portion 22a of the cutting tool cutting the sheet 130 of dense connective body tissue with a cookie cutter type action.

This results in a cylindrical opening being formed in the sheet 130 and in a body of dense connective body tissue 120 being disposed in the cutting tool 20a. The body of dense connective body tissue is removed from the cutting tool 20a with a suitable ejector (not shown). The body of dense connective body tissue 120 which is ejected from the cutting tool 20a will have a configuration corresponding to the configuration of the suture anchor 58a. It should be noted that the cutting tool 20a is reciprocated with a linear cutting and return stroke and is not rotated about its central axis as is the cutting tool 20 of FIG. 2.

If desired, the cutting tool 20a and thin elongated member 14a could be rotated together about their common central axis as they are moved into the body tissue 120. This would result in the same type of cutting action as is obtained with the separate thin elongated member 14 and cutting tool 20 of FIGS. 1 and 2. However, the rotating thin elongated member 14a and cutting tool 20a would cut the body tissue simultaneously rather than sequentially as in FIGS. 1 and 2.

It should be understood that a separate thin elongated member, corresponding to the thin elongated member 14 of FIGS. 1 and 2, and a rotatable cutting tool, corresponding to the cutting tool 20 could be utilized to cut the dense connective body tissue. If desired, the dense connective body tissue could have a configuration other than the configuration of the sheet 130. Thus, a relatively large block or piece of dense connective body tissue could be provided. Alternatively, the dense connective body tissue of the anchor 58a could be obtained directly from the patient's own body with the cutting tool 20a.

For example, the thin elongated member 14 could be inserted axially into the dense connective body tissue in the manner illustrated in FIG. 1 for the body tissue 12. The thin elongated member could be inserted into the dense connective body tissue while the thin elongated member is being rotated and pressed against the dense connective body tissue in the same manner as described in conjunction with the body tissue 12 of FIG. 1. The rotating cutting tool 20 will then cut a relatively long cylindrical core of dense connective body tissue. Once the core of dense connective body tissue has been removed from the cutting tool 20 and the thin elongated member 14, the cylindrical core of dense connective body tissue would be cut to a length corresponding to the desired length of the suture anchor 58a.

It is also contemplated that a suitable press could be utilized to shape the dense connective body tissue into the cylindrical configuration of the anchor 58a. Thus, a press having a construction similar to the construction disclosed in U.S. Pat. No. 5,329,846 issued Jul. 19, 1994 and entitled "Tissue Press and System" could be utilized to form the dense connective body tissue to a cylindrical configuration. If desired, the body tissue could be shaped around a thin elongated member which is subsequently withdrawn to form the passage 50a. Alternatively, the thin elongated member could be inserted into a cylindrical piece of dense connective body tissue to form the passage 50a after the body tissue has been removed from the press or while the body tissue is still in the press.

Once the suture anchor 58a has been formed, a suture is inserted into the passage 50a and the suture anchor is inserted into the body of a patient. The suture anchor 58a may be inserted to the body of a patient using an inserter assembly having the same construction as the inserter assembly 80 of FIGS. 4 and 5. Once the suture anchor 58a has been pushed into a patient's body, the suture is tensioned and force is applied against the trailing end of the suture anchor by the inner sleeve of the inserter to pivot the suture anchor in the manner illustrated schematically in FIG. 5. Of course, the suture anchor 58a may be inserted into either hard or soft body tissue in a manner which is different than the manner illustrated schematically in FIGS. 4 and 5 using an inserter assembly having a different construction than the inserter assembly 80.

Molded Suture Anchor

Figure 10:
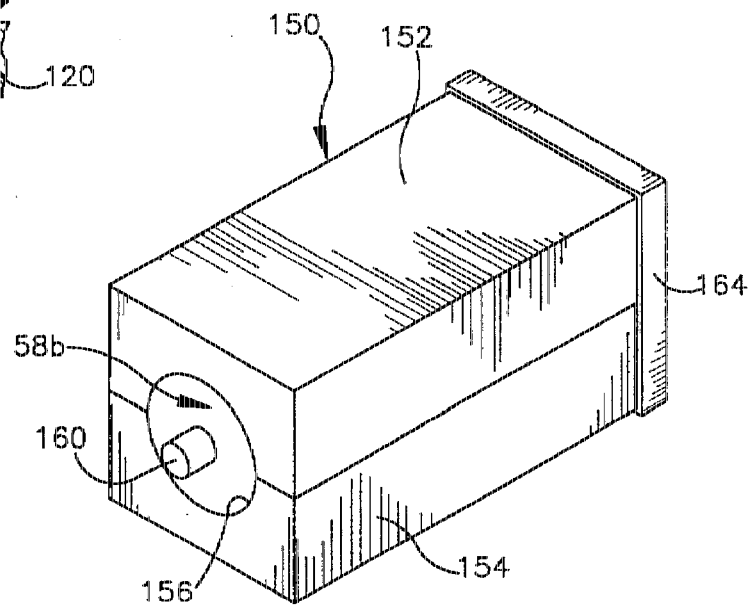
FIG. 10 is a schematic illustration depicting the manner in which a mold is used to shape body tissue to form an anchor.

In the embodiments of the invention illustrated in FIGS. 1–9, the suture anchors 58 and 58a were formed by cutting and/or pressing body tissue. In the embodiment of the invention illustrated in FIG. 10, the suture anchor is formed by molding body tissue. Since the embodiment of the invention illustrated in FIG. 10 is generally similar to the embodiments of the invention illustrated in FIGS. 1–9, similar numerals will be utilized to designate similar components, the suffix letter "b" being associated with the numerals of FIG. 10 to avoid confusion.

When a suture anchor 58b is to be formed, particles of body tissue, such as natural or artificial osseous body tissue, is positioned in a mold 150. The mold 150 includes upper and lower mold sections 152 and 154 which cooperate to define a cylindrical mold chamber 156. The cylindrical mold chamber 156 has a length corresponding to the desired axial extent of the suture anchor 58b. The mold chamber 156 has a diameter which corresponds to the desired diameter of the cylindrical outer side surface of the suture anchor 58b.

A cylindrical thin elongated member or core 160 extends axially through the mold chamber 156. An end plate 164 closes one end of the mold chamber 156 and supports one end of the core 160. A second end plate (not shown) closes the opposite end of the mold chamber 156 and supports the opposite end of the core 160.

Particles of bone and a suitable binder are conducted into the mold chamber. It is believed that it may be preferred to use fibrin as the binder. The natural or artificial bone particles are uniformly coated with the fibrin and completely fill the mold chamber 156. The fibrin is solidified around and interconnects the particles of body tissue to form the suture anchor 58b. It is contemplated that pressure may be applied against the mixture of binder and particles of body tissue in the mold 150 to compact the mixture.

Suture Anchor Formed of Dried Body Tissue

Regardless of which of the various body tissues and methods are utilized to form a suture anchor, it is contemplated that the body tissue may be dried. When a suture anchor formed of dried natural or artificial body tissue is inserted into a patient's body, the suture anchor is exposed to the fluid in the patient's body. The dried tissue of the suture anchor will absorb the fluid in the patient's body.

As the dried suture anchor absorbs the fluids in the patient's body, the suture anchor expands. As the suture anchor expands, it presses against the surrounding tissue of the patient's body and interlocks the suture anchor and the patient's body.

The suture anchor of dried body tissue can be inserted into an opening in a patient's body in the manner illustrated schematically for the suture anchor 58 in FIGS. 4 and 5. The suture anchor of dried body tissue is inserted into the recess 100 and is pivoted in the same manner as previously explained in conjunction with the embodiment of the invention illustrated in FIGS. 4 and 5. Once a suture anchor has been pivoted relative to the patient's body from the orientation shown in FIG. 4 through the orientation shown in FIG. 5 to the orientation shown in FIG. 6, the suture anchor absorbs body fluids and expands to more completely fill the recess 100.

It is contemplated that the suture anchor may be formed of many different types of dried body tissue. Thus, the suture anchor may be formed of dried osseous or bony body tissue. Alternatively, the suture anchor may be formed of dried dense connective body tissue, such as cartilage or tendon tissue. Although hard compact bone tissue may be dried, there will be relatively little expansion of the hard compact bone tissue when it is inserted into the patient's body.

When a suture anchor is formed of dried body tissue, the expansion or swelling of the suture anchor can be used to retain the suture anchor at a location where it would not be retained without expanding or swelling. Thus, a suture anchor formed of dried skin or other soft tissue may be inserted beneath the skin of the patient. The dried skin or other soft tissue forming the suture anchor will immediately begin to absorb the patient's body fluid (blood). As this occurs, the suture anchor will expand. Expansion of the suture anchor beneath the skin of the patient will prevent the suture anchor from being pulled back through the opening through which it was inserted beneath the skin of the patient.

Anchors formed of dried soft body tissue may be used at many different locations in a patient's body. For example, suture anchors formed of dried soft body tissue may be used in association with internal organs. The dried soft body tissue forming a suture anchor may be obtained from any one of many different sources. For example, body tissue may be obtained from inside a human other than the patient or from inside a non-human animal. This body tissue would be sterilized and dried before being formed into a suture anchor.

It is contemplated that the body tissue from which a suture anchor is to be formed may be dried in many different ways. Thus, the body tissue may be freeze dried. When a suture anchor is to be formed, a thin elongated member, corresponding to the thin elongated member 14 of FIG. 1, is inserted into the freeze dried body tissue. The cutting tool 20 is then rotated and moved axially along the thin elongated member to cut the freeze dried body tissue in the same manner illustrated schematically in FIG. 2.

Rather than freeze drying the body tissue, the body tissue could be dried by applying pressure against the body tissue and forcing fluid to flow from the body tissue. Thus, a press, similar to a press disclosed in U.S. Pat. No. 5,329,846 issued Jul. 19, 1994 and entitled "Tissue Press and System" may be utilized to apply pressure against body tissue and force fluid from the body tissue. When the body tissue is dried in this manner, the body tissue may be compressed to a cylindrical configuration with an outside diameter which corresponds to the outside diameter of a suture anchor.

A passage may be formed in the compressed and dried body tissue either before or after it is removed from the press. When the body tissue has been removed from the press, it can be further dried by being exposed to a warm dry environment. Alternatively, the body tissue may be dried without pressing, by exposing the body tissue to a warm dry environment for a sufficient length of time to result in evaporation of the fluid from the body tissue.

Conclusion

The present invention relates to a new and improved suture anchor 58 which is formed of body tissue. The body tissue is shaped to the desired configuration of the anchor 58. The body tissue defines a passage 50 through the anchor 58. A suture 62 is inserted into the passage 50 in the anchor 58. The anchor 58 and the suture 62 are inserted into a patient's body.

The anchor 58 may be formed of many different types of body tissue, including osseous body tissue, bone or dense connective tissue. The body tissue may be dried so that when the anchor 58 is exposed to fluid in a patient's body, the anchor absorbs the fluid and expands. The body tissue may be from the patient's own body, from another human, or from a nonhuman animal.

Having described the invention, the following is claimed:

1. A method of anchoring a suture, said method comprising the steps of forming an anchor of body tissue, said step of forming an anchor of body tissue includes forming an outer side surface of the anchor defined by body tissue while a thin member extends into the body tissue and, thereafter, removing the thin member from the body tissue to form a passage in the anchor, inserting a suture into the passage, and positioning the anchor formed of body tissue in a patient's body with the suture extending into the passage formed in the anchor.

2. A method as set forth in claim 1 wherein said step of forming an anchor of body tissue includes forming the anchor of osseous body tissue.

3. A method as set forth in claim 1 wherein said step of forming an anchor of body tissue includes forming an anchor of dried body tissue, said step of positioning the anchor formed of body tissue in a patient's body includes positioning the anchor at a location in the patient's body where the dried body tissue of the anchor is exposed to body fluid to enable the dried body tissue of the anchor to absorb body fluid.

4. A method as set forth in claim 1 wherein said step of forming an anchor of body tissue includes forming the anchor of body tissue which includes collagen.

5. A method as set forth in claim 1 wherein said step of forming an anchor of body tissue includes forming the anchor of interarticular fibrocartilage.

6. A method as set forth in claim 1 wherein said step of forming an anchor of body tissue includes forming the anchor from body tissue removed from the body of the patient, said step of positioning the anchor formed of body tissue in the patient's body includes positioning the anchor in the body of the patient from whom the body tissue forming the anchor was removed.

7. A method as set forth in claim 1 wherein said step of forming an anchor of body tissue includes forming the anchor from body tissue removed from a first human, said step of positioning the anchor formed of body tissue in a patient's body includes positioning the anchor in the body of a second human.

8. A method as set forth in claim 1 wherein said step of forming an anchor of body tissue includes forming the anchor from body tissue removed from an animal other than a human, said step of positioning the anchor formed of body tissue in a patient's body includes positioning the anchor in the body of a human.

9. A method as set forth in claim 1 wherein said step of positioning the anchor formed of body tissue in a patient's body with the suture extending into the passage includes moving the anchor formed of body tissue into the patient's body, and, thereafter pivoting the anchor relative to the patient's body.

10. A method as set forth in claim 9 wherein said step of pivoting the anchor includes tensioning the suture to apply force to the anchor.

11. A method as set forth in claim 11 wherein said step of forming an anchor of body tissue further includes moving the thin member into the body tissue, said step of forming an outer side surface of the anchor defined by body tissue includes moving a cutting tool along the thin member and cutting the body tissue with the cutting tool while moving the cutting tool along the thin member.

12. A method as set forth in claim 11 wherein said step of removing the thin member from the body tissue is performed after moving the cutting tool along the thin member and cutting the body tissue with the cutting tool.

13. A method as set forth in claim 1 wherein said step of forming an outer side surface of the anchor defined by body tissue includes compacting body tissue around the thin member.

14. A method as set forth in claim 1 wherein said step of forming an outer side surface of the anchor defined by body tissue includes forming a side surface of the anchor by cutting body tissue with a first cutting tool while the thin member extends into the body tissue, said step of forming an anchor of body tissue further includes cutting the body tissue with a second cutting tool to form an end surface of the anchor after having performed said step of removing the thin member from the body tissue.

15. A method as set forth in claim 1 wherein said step of forming an outer side surface of the anchor defined by body tissue includes forming a side surface of the anchor by cutting body tissue with a cutting tool, said method further including moving the thin member relative to the body tissue with the cutting tool while cutting body tissue with the cutting tool.

16. A method as set forth in claim 15 wherein said steps of cutting body tissue with a cutting tool and moving the thin member relative to the body tissue with the cutting tool includes simultaneously rotating the thin member and the cutting tool about a common axis.

17. A method as set forth in claim 15 wherein said steps of cutting body tissue with a cutting tool and moving the thin member relative to body tissue are performed with the thin member fixedly connected with the cutting tool to maintain a constant spatial relationship between the cutting tool and the thin member.

18. A method as set forth in claim 1 wherein said step of forming an outer side surface of the anchor defined by body tissue includes forming a cylindrical outer side surface having a central axis which is coincident with a central axis of the thin member.

19. A method as set forth in claim 1 wherein said step of forming an outer side surface of the anchor defined by body tissue includes applying pressure against the body tissue to shape the body tissue to a desired configuration.

20. A method as set forth in claim 1 wherein said step of forming an anchor of body tissue includes positioning the body tissue in a press and operating the press to apply pressure against the body tissue to shape the body tissue to a desired configuration.

21. A method as set forth in claim 1 wherein said step of forming an anchor of body tissue includes forming a sheet of body tissue, said step of forming an outer side surface of the anchor defined by body tissue includes cutting the sheet of body tissue with a cutting tool.

22. A method as set forth in claim 1 wherein said step of forming an anchor of body tissue further includes forming a piece of dried body tissue, said step of forming an outer side surface of the anchor defined by body tissue includes cutting the piece of dried body tissue.

23. A method as set forth in claim 22 wherein said step of forming a piece of dried body tissue includes compressing the body tissue to remove fluid from the body tissue.

24. A method as set forth in claim 1 further including the step of expanding the anchor under the influence of fluid absorbed from the patient's body after having performed said step of positioning the anchor formed of body tissue in the patient's body.

25. A method of anchoring a suture, said method comprising the steps of inserting a thin elongated member into osseous tissue, moving a cutting tool axially along the thin elongated member into engagement with the osseous tissue at a location spaced from the thin elongated member and extending around a portion of the thin elongated member, moving the cutting tool into the osseous tissue by cutting the osseous tissue with the cutting tool while continuing to move the cutting tool axially along the thin elongated member, said step of moving the cutting tool into the osseous tissue includes guiding movement of the cutting tool into the osseous tissue with the thin elongated member, separating a portion of the osseous tissue having an outer side surface formed by the cutting tool from the remainder of the osseous tissue, removing the thin elongated member from the osseous tissue to leave a passage at the location where the thin elongated member was inserted into the osseous tissue, inserting a suture into the passage in the osseous tissue, and inserting at least part of the portion of the osseous tissue having an outer side surface formed by the cutting tool and a portion of the suture into a patient's body with the suture extending into the passage in the osseous tissue.

26. A method as set forth in claim 25 further including the steps of tensioning the suture to transmit force from the suture to the osseous tissue having an outer side formed by the cutting tool, and transmitting force from the osseous tissue having an outer side formed by the cutting tool to the patient's body to retain a portion of the suture in the patient's body.

27. A method as set forth in claim 25 wherein said step of inserting a thin elongated member into osseous tissue includes inserting the thin elongated member into osseous tissue in the patient's body, said step of moving a cutting tool axially along the thin elongated member into engagement with the osseous tissue includes moving the cutting tool into engagement with osseous tissue in the patient's body, said step of separating a portion of the osseous tissue from the remainder of the osseous tissue includes removing the osseous tissue from the patient's body.

28. A method as set forth in claim 25 wherein said step of inserting a thin elongated member into osseous tissue includes inserting the thin elongated member into osseous tissue which is spaced from the patient's body, said step of moving a cutting tool axially along the thin elongated member into engagement with the osseous tissue includes moving the cutting tool into engagement with the osseous tissue which is spaced from the patient's body.

29. A method as set forth in claim 25 wherein said step of inserting a thin elongated member into osseous tissue includes rotating the thin elongated member about a longitudinal axis of the thin elongated member while pressing an end of the thin elongated member against the osseous tissue.

30. A method as set forth in claim 25 wherein said step of cutting the osseous tissue with the cutting tool includes rotating the cutting tool about a longitudinal axis of the thin elongated member.

31. A method as set forth in claim 25 further including cutting the portion of the osseous tissue separated from the remainder of the osseous tissue into a plurality of segments each of which has an outer side surface formed by the cutting tool, said step of inserting a suture into the passage in the osseous tissue includes inserting a suture through one of the segments of osseous tissue.

32. A method as set forth in claim 25 wherein said step of inserting a suture into the passage in the osseous tissue includes inserting the suture through the passage so that a first portion of the suture extends to a first end of the passage in the osseous tissue and a second portion of the suture extends from a second end of the passage in the osseous tissue, said step of inserting the portion of the osseous tissue having an outer side surface formed by the cutting tool and a portion of the suture into a patient's body is performed with the first and second portions of the suture extending from one side of a location where the portion of the osseous tissue is inserted into the patient's body to the first and second ends of the passage in the osseous tissue.

33. A method of anchoring a suture, said method comprising the steps of forming a piece of bone to have first and second circular ends, a cylindrical an outer side surface extending between said first and second ends, and a passage extending through the piece of bone from the first end to the second end, inserting a suture into the passage in the piece of bone, and inserting the piece of bone into body tissue with the first circular end of the piece of bone leading, with the second circular end of the piece of bone trailing, and with the suture extending from the passage in the piece of bone, said step of inserting the piece of bone into the body tissue includes applying force against the trailing second circular end of the piece of bone with an inserter member.

34. A method as set forth in claim 33 wherein said step of forming a piece of bone includes inserting a thin elongated member into a body of bone moving a cutting tool axially along the thin elongated member into the body of bone and cutting the body of bone with the cutting tool to form the outer side surface of the piece of bone as the cutting tool is moved into the body of bone.

35. A method as set forth in claim 34 wherein said step of forming a piece of bone includes disengaging the thin elongated member from the bone to leave a passage in the bone.

36. A method as set forth in claim 34 wherein the body of bone is spaced from a patient, said step of inserting the piece of bone into body tissue includes inserting the piece of bone into the patient's body.

37. A method as set forth in claim 34 wherein the body of bone is disposed in a patient's body, said step of inserting a thin elongated member into a body of bone includes inserting the thin elongated member into the patient's body, said step of forming a piece of bone includes removing bone from the patient's body, said step of inserting the piece of bone into body tissue includes inserting the piece of bone into the patient's body.

38. A method as set forth in claim 33 wherein said step of forming a piece of bone includes compressing a mixture of bone particles and a binder.

39. A method as set forth in claim 33 wherein said step of forming a piece of bone includes rotating a cutting tool and moving the cutting tool into bone along a path which extends parallel to an axis about which the cutting tool is rotated to at least partially form the outer side surface of the piece of bone.

40. A method as set forth in claim 39 wherein said step of forming a piece of bone includes rotating a thin elongated member and moving the thin elongated member into bone along a path which extends parallel to an axis about which the thin elongated member is rotated to at least partially form the passage which extends through the piece of bone.

41. A method as set forth in claim 40 wherein said steps of rotating a cutting tool and moving the cutting tool into bone and said steps of rotating a thin elongated member and moving the thin elongated member into bone are performed together.

42. A method as set forth in claim 40 wherein said steps of rotating a cutting tool and moving the cutting tool into bone are performed after performance of said step of rotating a thin elongated member and moving the thin elongated member into bone.

43. A method as set forth in claim 33 wherein said step of forming a piece of bone includes forming a piece of bone which is at least partially dried, said step of inserting the piece of bone into body tissue includes positioning the piece of bone in body tissue at a location where the piece of bone is exposed to body fluid to enable the piece of bone to absorb body fluid.

44. A method of anchoring a suture, said method comprising the steps of forming a cylindrical anchor of hard compact bone, said step of forming a cylindrical anchor of hard compact bone includes forming a core having a cylindrical outer side surface formed of hard compact bone and a passage extending through the core, said core having an axial extent which is greater than a desired length of the anchor, and cutting from the core a cylindrical piece of hard compact bone which has an axial extent corresponding to the desired length of the anchor and through which the passage axially extends, said method further including the steps of inserting a suture into the passage in the cylindrical piece of hard compact bone which forms the anchor, and positioning the cylindrical piece of hard compact bone which forms the anchor in a patient's body with the suture extending into the passage formed in the cylindrical piece of hard compact bone.

45. A method as set forth in claim 44 wherein said step of forming a core having a cylindrical outer side surface formed of hard compact bone and a passage extending through the core includes moving a thin member into the hard compact bone to form the passage and cutting the hard compact bone with a cutting tool while the thin member is disposed in the hard compact bone.

46. A method as set forth in claim 44 wherein said step of forming a core having a cylindrical outer side surface formed of hard compact bone and a passage extending through the core includes moving a thin member into the hard compact bone to form the passage and moving a cutting tool along the thin member to form the cylindrical outer side surface of the core with a longitudinal central axis of the cylindrical outer side surface of the core coincident with a central axis of the passage.

47. A method of anchoring a suture, said method comprising the steps of inserting a thin elongated member into hard compact bone, moving a rotating cutting tool into the hard compact bone by cutting the hard compact bone with the rotating cutting tool while the thin elongated member extends into the hard compact bone, removing the thin elongated member from the hard compact bone to leave a passage at the location where the thin elongated member was inserted into the hard compact bone, inserting a suture into the passage in the hard compact bone, and inserting the hard compact bone having an outer side surface formed by the cutting tool and a portion of the suture into a patient's body with the suture extending into the passage in the hard compact bone.

48. A method as set forth in claim 47 further including the steps of tensioning the suture to transmit force from the suture to the hard compact bone having an outer side formed by the cutting tool, and transmitting force from the hard compact bone having an outer side formed by the rotating cutting tool to the patient's body to retain a portion of the suture in the patient's body.

49. A method as set forth in claim 47 wherein said step of inserting a thin elongated member into hard compact bone includes inserting the thin elongated member into hard compact bone in the patient's body, said step of moving a rotating cutting tool into engagement with the hard compact bone includes moving the rotating cutting tool axially along the thin elongated member into engagement with hard compact bone in the patient's body.

50. A method as set forth in claim 47 wherein said step of inserting a thin elongated member into hard compact bone includes simultaneously rotating the thin elongated member and cutting tool about a longitudinal axis of the thin elongated member while pressing an end of the thin elongated member against the hard compact bone.

51. A method of anchoring a suture, said method comprising the steps of forming an anchor of body tissue, said step of forming an anchor of body tissue includes rotating a thin elongated member and a cutting tool together about a longitudinal axis of the thin elongated member, simultaneously moving the rotating cutting tool and rotating thin elongated member into the body tissue, forming a cylindrical outer side surface of a core of body tissue with the rotating cutting tool as the rotating cutting tool is moved into the body tissue, forming a passage extending axially through the core of body tissue with the rotating thin elongated member as the rotating thin elongated member is moved into the body tissue, removing the core of body tissue from body tissue from which the core was cut by the rotating cutting tool, said core of body tissue having an axial extent which is greater than a desired length of the anchor, removing the thin elongated member from the core of body tissue to form a passage extending through the core of body tissue, and cutting from the core of body tissue a cylindrical piece of body tissue having an axial extent corresponding to the desired length of the anchor and through which the passage extends, said method further including the steps of inserting a suture into the passage formed in the cylindrical piece of body tissue which forms the anchor, and positioning the cylindrical piece of body tissue which forms the anchor in a patient's body with the suture extending into the passage formed in the cylindrical piece of body tissue, said step of positioning the cylindrical piece of body tissue which forms the anchor in a patient's body includes applying force against a trailing end of the anchor with a tubular inserter member having a passage through which a first portion of the suture extends and pivoting the anchor relative to the tubular inserter member by tensioning a second portion of the suture to apply force to a leading end of the anchor.

52. A method as set forth in claim 51 further including the step of drying the body tissue prior to performance of said step of forming an anchor of body tissue, said step of positioning the cylindrical piece of body tissue which forms the anchor in a patient's body includes positioning the anchor at a location in the patient's body where the anchor is exposed to the patient's body fluid to enable the anchor to absorb the patient's body fluid and expand in the patient's body.

* * * * *

UNITED STATES PATENT AND TRADEMARK OFFICE
CERTIFICATE OF CORRECTION

PATENT NO. : 5 713 921
DATED : February 3, 1998
INVENTOR(S) : Peter M. Bonutti

It is certified that error appears in the above-indentified patent and that said Letters Patent is hereby corrected as shown below:

Column 12, line 4, change "11" to --1--.

Column 14, line 23, after "cylindrical" delete --an--.

Column 14, line 40, after "of" delete --.--.

Signed and Sealed this

Eighth Day of September, 1998

Attest:

BRUCE LEHMAN

Attesting Officer

Commissioner of Patents and Trademarks